| United States Patent [19] | [11] 4,075,227 |
|---|---|
| Jones et al. | [45] Feb. 21, 1978 |

[54] ANTIFERTILITY COMPOUNDS

[75] Inventors: C. David Jones; Tulio Suarez, both of Indianapolis, Ind.

[73] Assignee: Eli Lilly and Company, Indianapolis, Ind.

[21] Appl. No.: 743,819

[22] Filed: Nov. 22, 1976

Related U.S. Application Data

[63] Continuation-in-part of Ser. No. 626,009, Oct. 28, 1975, abandoned.

[51] Int. Cl.² .................. C07D 333/56; C07D 333/64
[52] U.S. Cl. ............................ 260/330.5; 260/293.57;
260/306.7 R; 260/326.5 SA; 260/519; 260/571;
260/590 D; 424/267; 424/274; 424/275;
424/248.51; 544/146

[58] Field of Search ..................................... 260/330.5

[56] References Cited

U.S. PATENT DOCUMENTS

| 3,947,470 | 3/1976 | Brenner et al. .................. 260/330.5 |
| 3,983,245 | 9/1976 | Ladd et al. ............................ 424/285 |
| 4,001,426 | 1/1977 | Brenner et al. ...................... 424/285 |
| 4,007,204 | 2/1977 | Descamps et al. ............... 260/330.5 |

*Primary Examiner*—Cecilia M. S. Jaisle
*Attorney, Agent, or Firm*—William C. Martens, Jr.; Arthur R. Whale

[57] ABSTRACT

Derivatives of 2-aroyl-3-phenylbenzothiophenes and 2-aroyl-3-phenylbenzothiophene-1-oxides are useful as antifertility agents.

8 Claims, No Drawings

ANTIFERTILITY COMPOUNDS

CROSS REFERENCE

This application is a continuation-in-part of Application Ser. No. 626,009 filed Oct. 28, 1975 now abandoned.

BACKGROUND OF THE INVENTION

This invention relates to novel compounds. More particularly, this invention relates to novel compounds which possess valuable utility as antifertility agents and thus are useful in the control of animal populations. In another aspect, this invention relates to a novel method of inhibiting pregnancy and to a novel method of controlling animal populations.

The prior art has recognized various classes of compounds, each having the general formula

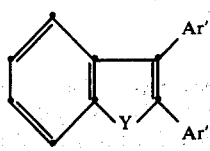

in which Ar is an aryl moiety and Y is any of various groups, such as $-CH_2-$, $-CH_2-CH_2-$, $-S-$, $-NH$, $-OCH_2-$, $-O-$, $-CH_2S-$, and $-SCH_2-$. Many compounds within these general classes are described as having antifertility activity.

Lednicer et al., *J. Med. Chem.*, 8, (1965), pp. 52–57, discloses 2,3-diphenylindenes and derivatives thereof as antifertility agents.

Lednicer et al., *J. Med. Chem.*, 9, (1966), pp. 172–175; Lednicer et al., *J. Med. Chem.*, 10 (1967), pp. 78–84; and Bencze et al., *J. Med. Chem.*, 8 (1965), pp. 213–214, each disclose various 1,2-diaryl-3,4-dihydronaphthalenes as active antifertility agents. In addition, U.S. Pat. Nos. 3,274,213; 3,313,853; 3,396,169; and 3,567,737 disclose various 1,2-diphenyl-3,4-dihydronaphthalenes as useful antifertility agents.

Other United States Patents disclose both 1,2-diphenyl-3,4-dihydronaphthalenes and 2,3-diphenylindenes as active agents. These include U.S. Pat. Nos. 3,293,263; 3,320,271; 3,483,293; 3,519,675; 3,804,851; and 3,862,232.

In addition, Crenshaw et al., *J. Med. Chem.* 14, (1971), pp. 1185–1190, discloses, among others, various 2,3-diarylbenzothiophenes as exhibiting antifertility activity. Certain of these compounds are claimed in U.S. Pat. No. 3,413,305. Crenshaw et al. additionally disclose other compounds which participate in the general classes described hereinabove. 2,3-Diarylbenzofurans corresponding generally to the above benzothiophenes are disclosed and claimed in U.S. Pat. No. 3,394,125.

A need still exists to provide additional compounds useful as antifertility agents and, in particular, nonsteroidal antifertility agents. The novel compounds of this invention fill such a need. They are 2-aroyl-3-phenylbenzothiophenes and 2-aroyl-3-phenylbenzothiophene-1-oxides, and, structurally, they differ significantly from those described in the aforementioned prior art. It is an object therefore of this invention to provide novel nonsteroidal compounds having antifertility activity.

SUMMARY OF THE INVENTION

This as well as other objects are achieved by this invention which comprises a class of compounds having the formula

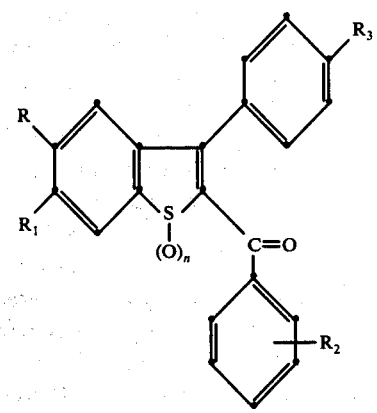

in which $n$ is 0 or 1; R and $R_1$ independently are hydrogen, hydroxyl, $C_1$- to $C_5$-alkoxy, or $C_5$- to $C_6$-cycloalkoxy; subject to the limitation that at least one of R and $R_1$ is hydrogen; $R_2$ is hydrogen, chloro, bromo, hydroxyl, $C_1$- to $C_5$-alkoxy, or $C_5$- to $C_6$-cycloalkoxy; subject to the limitation that at least one of R, $R_1$, or $R_2$ is other than hydrogen; and $R_3$ is hydrogen or

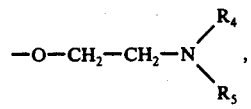

in which $R_4$ and $R_5$ independently are $C_1$–$C_4$ alkyl, or $R_4$ and $R_5$ taken together with the nitrogen to which they are bonded constitute a heterocycle selected from the group consisting of pyrrolidino, piperidino, hexamethyleneimino, or morpholino; and pharmaceutically acceptable non-toxic acid addition salts of those compounds in which

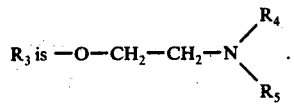

As indicated above, this invention also includes the pharmaceutically acceptable non-toxic acid addition salts of those of the above compounds in which

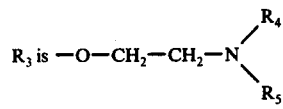

The pharmaceutically acceptable non-toxic acid addition salts include the organic and inorganic acid addition salts, for example, those prepared from acids such as hydrochloric, sulfuric, sulfonic, tartaric, fumaric, hydrobromic, glycolic, citric, maleic, phosphoric, succinic, acetic, nitric, and the like. Preferably, the acid addition salts are those prepared from citric acid. Such salts are prepared by conventional methods.

The term "$C_1$–$C_4$ alkyl" as used herein contemplates both straight and branched chain groups such as methyl, ethyl, n-propyl, isopropyl, n-butyl, t-butyl, isobutyl, and sec-butyl.

The term "$C_1$-$C_5$ alkoxy" as used herein contemplates both straight and branched chain alkyl radicals and therefore defines groups such as, for example, methoxy, ethoxy, n-propoxy, isopropoxy, n-butyloxy, isobutyloxy, t-butyloxy, sec-butyloxy, n-amyloxy, isoamyloxy, t-amyloxy, sec-amyloxy, and the like.

The term "$C_5$-$C_6$ cycloalkoxy" as used herein contemplates cyclopentyloxy and cyclohexyloxy.

A preferred subclass of the compounds of this invention are the benzothiophenes, that is, in the above formula, those compounds in which $n$ is zero.

Of the defined benzothiophenes, several preferred subclasses exist. One such subclass is comprised of the 6-hydroxybenzothiophenes, that is, those compounds in which $n$ is zero and $R_1$ is hydroxyl.

Another such subclass includes the 2-(4-hydroxybenzoyl)benzothiophenes, that is, those compounds in which $n$ is zero and $R_2$ is a hydroxyl group located in the position para to the carbonyl function.

A further preferred subclass includes the 3-[4-(2-disubstitutedaminoethoxy)phenyl]benzothiophenes, that is, those compounds in which $n$ is zero and

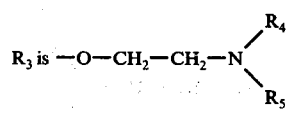

When $R_3$ is so defined, it is further preferred that both $R_4$ and $R_5$ are methyl, both $R_4$ and $R_5$ are ethyl, or $R_4$ and $R_5$ taken together with the nitrogen to which they are bonded constitute a pyrrolidino ring.

The compounds of this invention are prepared by several routes, the major differences, in general, being dependent upon the identities of $n$, R, and $R_1$ in the foregoing formula.

A. Preparation of compounds in which $n$ is O and R is hydrogen. A thiol of the formula

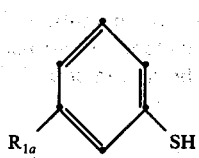

in which $R_{1a}$ is hydrogen, $C_1$- to $C_5$-alkoxy, $C_5$- to $C_6$-cycloalkoxy, phenacyloxy, or p-halophenacyloxy is reacted with an α-haloacetophenone of the formula

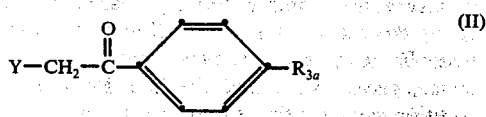

in which $R_{3a}$ is hydrogen or hydroxyl, and Y is halogen to produce the compound

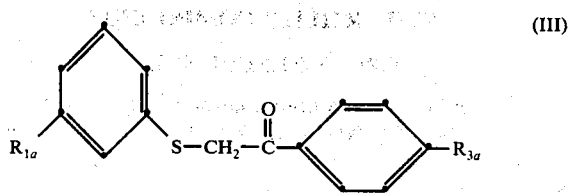

This product is ring-closed in the presence of an acid, such as an aryl sulfonic acid, an alkane sulfonic acid, sulfuric acid, polyphosphoric acid, and the like, to the corresponding benzothiophene of the formula

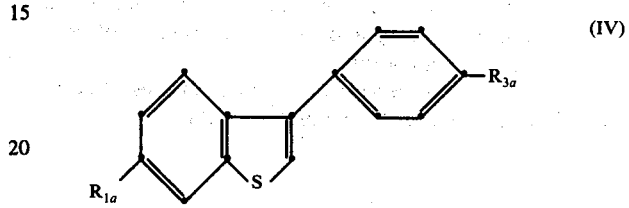

The benzothiophene (IV) then is reacted in the presence of a Friedel-Crafts catalyst, such as aluminum chloride, with a benzoyl chloride of the formula

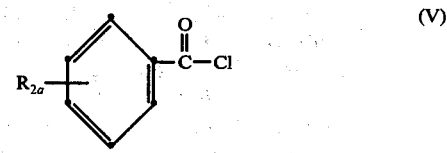

in which $R_{2a}$ is hydrogen, chloro, bromo, $C_1$- to $C_5$-alkoxy, $C_5$- to $C_6$-cycloalkoxy, phenacyloxy, or p-halophenacyloxy, to produce

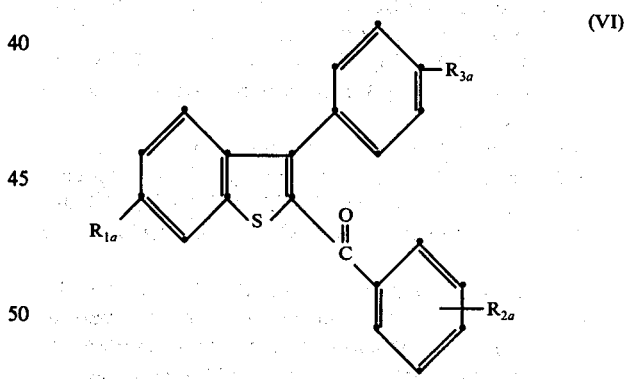

a compound of this invention.

The compound (VI) can readily be converted to other compounds within the series.

When it is desired that $R_{1a}$ and/or $R_{2a}$ be hydroxy, such is available from the corresponding alkoxy compound by treatment of the latter with pyridine hydrochloride at a temperature of from about 200° C, to about 250° C. Other reagents which can be employed include boron tribromide, sodium thioethoxide, and hydrogen bromide.

Alternatively, $R_{1a}$ and/or $R_{2a}$ can be phenacyloxy or p-halophenacyloxy, such as p-chlorophenacyloxy or p-bromophenacyloxy. Any of these phenacyl groups are suitable as protecting groups, being readily cleaved upon treatment with zinc and acetic acid at about 60° C.

for approximately one hour to form the corresponding hydroxy compound. The particular sequence of synthetic steps designed to produce a compound having substituents of particular definition and location is such as one of ordinary skill in the art will well recognize.

Compounds in which R₃ is

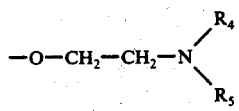

are available from the corresponding hydroxy compound by treatment thereof in the presence of a moderately strong base, such as sodium hydroxide, with a compound of the formula

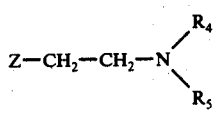

in which Z is halo, particularly bromo or chloro.

B. Preparation of compounds in which $n$ is O and R is other than hydrogen.

The preparation of 5-substituted benzothiophenes of this invention is somewhat more complex than the preparation of their 6-substituted counterparts. The former compounds can be prepared by a sequence such as the following:

A ketone of the formula

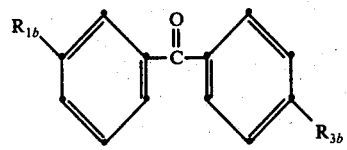

in which $R_{1b}$ is $C_1$-to $C_5$-alkoxy, $C_5$- to $C_6$-cycloalkoxy, phenacyloxy, or p-halophenacyloxy, and $R_{3b}$ is hydrogen or hydroxyl is reacted with ammonia in the presence of titanium tetrachloride to produce the corresponding ketimine of the formula

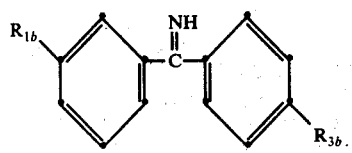

The ketimine is treated with rhodanine

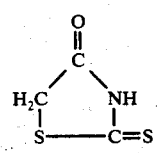

under acidic conditions to produce an isomeric mixture of

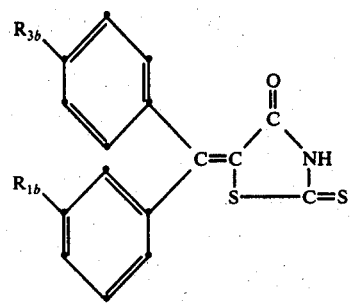

which then is converted under alkaline conditions to a substituted cinnamic acid of the formula

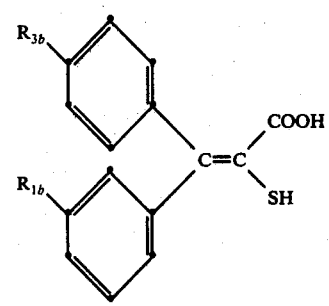

The cinnamic acid is ring-closed by treatment with chlorine to produce a 5-substituted 2-carboxybenzothiophene of the formula

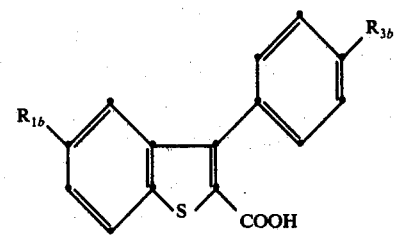

It is apparent that the described ring-closure can occur in either of two directions, and thus two different products are available. However, the desired benzothiophene (XI) is found as one of the products of the above reaction and is readily separated from other products by recognized procedures.

The 2-carboxybenzothiophene (XI) is converted to its corresponding acid halide by reaction, for example, with thionyl chloride.

Treatment of the acid halide in the presence of aluminum chloride with

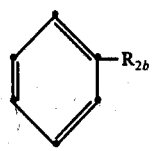

in which $R_{2b}$ is hydrogen, chloro, bromo, $C_1$- to $C_5$-alkoxy, $C_5$- to $C_6$-cycloalkoxy, phenacyloxy, or p-halophenacyloxy produces a 5-substituted benzothiophene of this invention.

The product can be modified by employing the same derivatizing reactions described hereinabove to prepare other compounds within the scope of this invention.

C. Preparation of compounds in which n is 1.

These compounds are readily available by oxidation of any of the benzothiophenes produced as described above. Oxidation can be carried out by treating the benzothiophene with an oxidizing agent, for example, m-chloroperbenzoic acid, or the like, for a time sufficient to achieve formation of the sulfoxide group. The ongoing of the reaction can be monitored by standard thin-layer chromatography (TLC) methods.

The compounds of this invention are valuable pharmaceutical agents. They exhibit anti-fertility activity, and they especially are useful as orally active antifertility agents in birds and mammals. The compounds of this invention thus are useful in controlling the animal population and as contraceptives in living beings. The compounds of this invention also are valuable for animal pest control. For example, the compounds of this invention can be formulated in combination with baits and/or attractants and placed in feeding stations accessible to undesirable rodents and other small animals including Canidae such as coyotes, foxes, wolves, jackals, and wild dogs, and birds, such as starlings, galls, redwing blackbirds, pigeons, and the like, to greatly reduce the population thereof. By reason of the activity of the compounds of this invention, they can be used to reduce hazards to aviation by lessening the presence of birds and animals on runaways and in the vicinity of air fields. The compounds of this invention also can be used to reduce the population of undesirable birds and animals so as to aid in the prevention and the spread of disease, and to reduce the destruction of property in both rural and urban areas.

The compounds of this invention can be administered as such, or they can be compounded and formulated into pharmaceutical preparations in unit dosage form for oral or parenteral administration. In the compounding or formulation, organic or inorganic solids and/or liquids which are pharmaceutically acceptable carriers can be employed. Suitable such carriers will be well recognized by those of ordinary skill in the art. The compositions may take the form of tablets, powder granules, capsules, suspensions, solutions, and the like.

The compounds of this invention, when administered in an effective amount, will produce the inhibition of pregnancy in mammals. The usual daily dose is from about 0.04 milligrams to about 20 milligrams per kilogram body weight of the recipient. The preferred daily dose is from about 0.04 milligrams to about 0.4 milligrams per kilogram body weight of the recipient.

Examples of compounds of this invention include the following:

2-(3-hydroxybenzoyl)-3-phenylbenzothiophene;
2-(2-methoxybenzoyl)-3-phenylbenzothiophene;
2-(4-chlorobenzoyl)-3-phenylbenzothiophene;
2-(3-bromobenzoyl)-3-phenylbenzothiophene;
2-(4-isopropoxybenzoyl)-3-phenylbenzothiophene;
2-(3-t-butyloxybenzoyl)-3-phenylbenzothiophene;
2-(4-pentyloxybenzoyl)-3-phenylbenzothiophene;
2-(3-cyclopentyloxybenzoyl)-3-phenylbenzothiophene;
2-(4-cyclohexyloxybenzoyl)-3-phenylbenzothiophene;
2-(3-ethoxybenzoyl)-3-phenylbenzothiophene;
2-(2-hydroxybenzoyl)-3-[4-(2-hexamethylene-iminoethoxy)phenyl]benzothiophene;
2-(3-methoxybenzoyl)-3-[4-(2-dimethylaminoethoxy)phenyl]benzothiophene;
2-(2-isopropoxybenzoyl)-3-[4-(2-diethylaminoethoxy)phenyl]benzothiophene;
2-(4-t-butyloxybenzoyl)-3-[4-(2-pyrrolidinoethoxy)phenyl]benzothiophene;
2-(3-pentyloxybenzoyl)-3-[4-(2-piperidinoethoxy)phenyl]benzothiophene;
2-(4-cyclopentyloxybenzoyl)-3-[4-(2-morpholinoethoxy)phenyl]benzothiophene;
2-(3-cyclohexyloxybenzoyl)-3-[4-(2-pyrrolidinoethoxy)phenyl]benzothiophene;
2-(4-chlorobenzoyl)-3-[4-(2-dimethylaminoethoxy)phenyl]benzothiophene;
2-(3-bromobenzoyl)-3-[4-(2-diethylaminoethoxy)phenyl]benzothiophene;
2-(4-methoxybenzoyl)-3-[4-(2-pyrrolidinoethoxy)phenyl]benzothiophene;
2-(3-hydroxybenzoyl)-3-[4-(2-piperidinoethoxy)phenyl]benzothiophene;
2-(4-hydroxybenzoyl)-3-[4-(2-morpholinoethoxy)phenyl]benzothiophene;
2-(4-hydroxybenzoyl)-3-phenyl-5-hydroxybenzothiophene;
2-(4-methoxybenzoyl)-3-phenyl-6-methoxybenzothiophene;
2-(4-isopropoxybenzoyl)-3-phenyl-5-ethoxybenzothiophene;
2-(3-t-butyloxybenzoyl)-3-phenyl-6-propoxybenzothiophene;
2-(4-pentyloxybenzoyl)-3-phenyl-6-cyclohexyloxybenzothiophene;
2-(3-cyclopentyloxybenzoyl)-3-phenyl-6-hydroxybenzothiophene;
2-(4-cyclohexyloxybenzoyl)-3-phenyl-5-ethoxybenzothiophene;
2-benzoyl-3-phenyl-6-methoxybenzothiophene;
2-benzoyl-3-phenyl-6-hydroxybenzothiophene;
2-benzoyl-3-[4-(2-hexamethyleneiminoethoxy)phenyl]-6-methoxybenzothiophene;
2-benzoyl-3-[4-(2-pyrrolidinoethoxy)phenyl]-5-hydroxybenzothiophene;
2-benzoyl-3-[4-(2-piperidinoethoxy)phenyl]-6-ethoxybenzothiophene;
2-benzoyl-3-[4-(2-morpholinoethoxy)phenyl]-6-methoxybenzothiophene;
2-benzoyl-3-phenyl-5-cyclopentyloxybenzothiophene;
2-benzoyl-3-phenyl-6-pentyloxybenzothiophene;
2-benzoyl-3-phenyl-5-isopropoxybenzothiophene;
2-benzoyl-3-phenyl-6-isopropoxybenzothiophene;
2-benzoyl-3-[4-(2-hexamethyleneiminoethoxy)phenyl]-5-butyloxybenzothiophene;
2-benzoyl-3-phenyl-5-hydroxybenzothiophene;
2-(3-hydroxybenzoyl)-3-phenylbenzothiophene-1-oxide;
2-(2-methoxybenzoyl)-3-phenylbenzothiophene-1-oxide;
2-(4-isopropoxybenzoyl)-3-phenylbenzothiophene-1-oxide;
2-(3-t-butyloxybenzoyl)-3-phenylbenzothiophene-1-oxide;
2-(4-pentyloxybenzoyl)-3-phenylbenzothiophene-1-oxide;
2-(2-chlorobenzoyl)-3-phenylbenzothiophene-1-oxide;
2-(4-bromobenzoyl)-3-phenylbenzothiophene-1-oxide;

2-(3-cyclopentyloxybenzoyl)-3-phenylbenzothiophene-1-oxide;

2-(4-cyclohexyloxybenzoyl)-3-phenylbenzothiophene-1-oxide;

2-(3-ethoxybenzoyl)-3-phenylbenzothiophene-1-oxide;

2-(2-hydroxybenzoyl)-3-[4-(2-hexamethyleneiminoethoxy)phenyl]benzothiophene-1-oxide;

2-(3-methoxybenzoyl)-3-[4-(2-dimethylaminoethoxy)phenyl]benzothiophene-1-oxide;

2-(2-isopropoxybenzoyl)-3-[4-(2-diethylaminoethoxy)phenyl]benzothiophene-1-oxide;

2-(4-t-butyloxybenzoyl)-3-[4-(2-pyrrolidinoethoxy)phenyl]benzothiophene-1-oxide;

2-(3-pentyloxybenzoyl)-3-[4-(2-piperidinoethoxy)phenyl]benzothiophene-1-oxide;

2-(4-cyclopentyloxybenzoyl)-3-[4-(2-morpholinoethoxy)phenyl]benzothiophene-1-oxide;

2-(3-cyclohexyloxybenzoyl)-3-[4-(2-pyrrolidinoethoxy)phenyl]benzothiophene-1-oxide;

2-(4-chlorobenzoyl)-3-[4-(2-dimethylaminoethoxy)phenyl]benzothiophene-1-oxide;

2-(3-bromobenzoyl)-3-[4-(2-diethylaminoethoxy)phenyl]benzothiophene-1-oxide;

2-(4-methoxybenzoyl)-3-[4-(2-pyrrolidinoethoxy)phenyl]benzothiophene-1-oxide;

2-(3-hydroxybenzoyl)-3-[4-(2-piperidinoethoxy)phenyl]benzothiophene-1-oxide;

2-(4-hydroxybenzoyl)-3-[4-(2-morpholinoethoxy)phenylbenzothiophene-1-oxide;

2-(4-hydroxybenzoyl)-3-phenyl-5-hydroxybenzothiophene-1-oxide;

2-(4-methoxybenzoyl)-3-phenyl-6-methoxybenzothiophene-1-oxide;

2-(4-isopropoxybenzoyl)-3-phenyl-5-ethoxybenzothiophene-1-oxide;

2-(3-t-butyloxybenzoyl)-3-phenyl-6-propoxybenzothiophene-1-oxide;

2-(4-pentyloxybenzoyl)-3-phenyl-6-cyclohexyloxybenzothiophene-1-oxide;

2-(3-cyclopentyloxybenzoyl)-3-phenyl-6-hydroxybenzothiophene-1-oxide;

2-(4-cyclohexyloxybenzoyl)-3-phenyl-5-ethoxybenzothiophene-1-oxide;

2-benzoyl-3-phenyl-6-methoxybenzothiophene-1-oxide;

2-benzoyl-3-phenyl-6-hydroxybenzothiophene-1-oxide;

2-benzoyl-3-[4-(2-hexamethyleneiminoethoxy)phenyl]-6-methoxybenzothiophene-1-oxide;

2-benzoyl-3-[4-(2-pyrrolidinoethoxy)phenyl]-5-hydroxybenzothiophene-1-oxide;

2-benzoyl-3-[4-(2-piperidinoethoxy)phenyl]-6-ethoxybenzothiophene-1-oxide;

2-benzoyl-3-[4-(2-morpholinoethoxy)phenyl]-6-methoxybenzothiophene-1-oxide;

2-benzoyl-3-phenyl-5-cyclopentyloxybenzothiophene-1-oxide;

2-benzoyl-3-phenyl-6-pentyloxybenzothiophene-1-oxide;

2-benzoyl-3-phenyl-5-ethoxybenzothiophene-1-oxide;

2-benzoyl-3-phenyl-6-isopropoxybenzothiophene-1-oxide;

2-benzoyl-3-[4-(2-hexamethyleneiminoethoxy)phenyl]-5-butyloxybenzothiophene-1-oxide;

2-benzoyl-3-phenyl-5-hydroxybenzothiophene-1-oxide;

The following examples are provided for the purpose of illustrating the preparation and pharmaceutical activity of the compounds of this invention. They are not intended to be limiting upon the broad scope thereof.

PREPARATION OF TYPICAL KEY INTERMEDIATES

A. 3-Phenylbenzothiophene

To 300 ml. of pyridine were added 150 g. (0.75 mole) of α-bromoacetophenone and 83 g. (0.75 mole) of thiophenol. The mixture was heated at reflux for six hours. The pyridine then was evaporated, and the residue was dissolved in ethyl acetate. The ethyl acetate solution was washed exhaustively with 1N sodium hydroxide and 1N hydrochloric acid, dried over magnesium sulfate, filtered, and evaporated to a brown oil. The brown oil was crystallized from alcohol at 0° C. to give 116 g. (68 percent) of α-(phenylthio)acetophenone as white crystals, m.p. 52°–53° C.

Analysis, Calcd. for $C_{14}H_{12}OS$: C, 73.65; H, 5.30; O, 7.01; S, 14.04. Found: C, 73.46; H, 5.50; O, 7.25; S, 14.30.

The above product was cyclized by heating it in polyphosphoric acid on a steam bath at 90° C. for two hours. From the product mixture was obtained crude product which was chromatographed on silica using a mixture of petroleum ether and benzene to obtain 3-phenylbenzothiophene as pure product.

B. 3-Phenyl-6-methoxybenzothiophene

To 200 ml. of pyridine were added 50 g. (0.357 mole) of 3-methoxythiophenol and 70.98 g. (0.357 mole) of α-bromoacetophenone. The mixture was refluxed for six hours. The resulting clear yellow solution was cooled and evaporated to dryness. The residue was dissolved in ethyl acetate and washed exhaustively with 1N hydrochloric acid, 1N sodium hydroxide, and water. The ethyl acetate solution then was dried over magnesium sulfate, filtered, and evaporated to give a yellow oil. The yellow oil was crystallized from a cooled alcohol solution thereof to give 63 g. (68 percent) of α-(3-methoxyphenylthio)acetophenone, m.p. 46°–47° C. The nmr spectrum was consistent with the structure of the product.

Analysis, Calcd. for $C_{15}H_{14}O_2S$: C, 69.74; H, 5.46; O, 12.39; S, 12.41. Found: C, 69.56; H, 5.76; O, 12.65; S, 12.28.

To 300 ml. of concentrated sulfuric acid were added 22 g. of the above product. The mixture was maintained at 25° C. for 15 minutes. The resulting red solution was poured over ice, and the product was extracted in ethyl acetate. The ethyl acetate extract was washed with water until neutral, dried, and evaporated to give a colorless oil which crystallized on standing. Recrystallization from alcohol gave 13 g. (64 percent) of 3-phenyl-6-methoxybenzothiophene as white crystals, m.p. 58°–59° C. C. 3-(4-Hydroxyphenyl)-6-methoxybenzothiophene To 100 g. (0.713 mole) of 3-methoxythiophenol in 200 ml. of ethanol were added 40.4 g. (0.72 mole) of potassium hydroxide. A solution of 121.7 g. (0.713 mole) of α-chloro-4-hydroxyacetophenone in 700 ml. of ethanol was rapidly added to the resulting mixture. The mixture was stirred for 30 minutes. The bulk of the ethanol was evaporated, and the resulting brown residue was poured into 3 liters of water. The mixture was shaken vigorously with formation of brown lumps of crystals. The brown lumps were homogenized in a blender, with addition of more water. The crystals, now tan in color, were collected, air dried, and recrystallized twice from 300 ml. of methanol. The light tan crystals were vacuum dried at 40° C to give 147.2 g. (76 percent) of α-(3-methoxyphenylthio)-4-hydroxyacetophenone, M.p. 107°-108° C.

Analysis, Calcd. for $C_{15}H_{14}O_3S$: C, 65.67; H, 5.14; O, 17.50; S, 11.69. Found: C, 64.02; H, 5.30; O, 18.12; S, 11.93.

To 80 ml. of methanesulfonic acid (cooled to about 15° C.) were added 20.0 g. of the above product. The resulting mixture was stirred for two hours, and the dark red solution was poured over about 2 liters of ice. The mixture was extracted with 1 liter of ether. The ether extract was washed twice with 100 ml. of aqueous sodium chloride solution and once with 100 ml. of aqueous sodium bicarbonate solution. The ether layer was dried over magnesium sulfate, filtered, and evaporated to give an oil. The oil was crystallized from a mixture of ether and hexane to obtain 12.0 g. of 3-(4-hydroxyphenyl)-6-methoxybenzothiophene as white crystals, m.p. 140°-140.5° C.

EXAMPLE 1

Preparation of 2-(4-Methoxybenzoyl)-3-phenylbenzothiophene.

To a stirred slurry of 14.6 g. (0.11 mole) of aluminum chloride in 1,2-dichloroethane maintained at 0° C. were added 18.7 g. (0.11 mole) of 4-methoxybenzoyl chloride. The mixture was stirred at 0° C. for 10 minutes, and 21.0 g. (0.1 mole) of 3-phenylbenzothiophene in 1,2-dichloroethane were added. The mixture was stirred for two hours, the temperature being maintained at 0° C. The reaction mixture then was poured into a mixture of hydrochloric acid in ice. The resulting mixture was extracted with ether. The ether extract was washed with water, dilute aqueous sodium bicarbonate, and water. The ether layer was dried over magnesium sulfate, and the ether solvent was evaporated. The residue was dissolved in ethanol. The ethanol solution was filtered and maintained at 5° C. for three days. The resulting crystals were filtered and washed with ethanol and petroleum ether to obtain 23.7 g. (70 percent) of the title compound, m.p. 94°-95° C. The nmr spectrum was consistent with the structure of the title compound.

Analysis, Calcd. for $C_{22}H_{16}O_2S$: C, 76.72; H, 4.68; O, 9.29. Found: C, 76.54; H, 4.74; O, 9.25.

EXAMPLE 2

Preparation of 2-(4-Methoxybenzoyl)-3-phenylbenzothiophene-1-oxide.

The product from Example 1 (8.2 g,; 0.0238 mole) dissolved in chloroform was cooled in an ice-ethanol bath, and 4.5 g. (0.026 mole) of m-chloroperbenzoic acid in chloroform were added dropwise. The mixture was stirred at room temperature overnight. The resulting mixture then was washed successively with aqueous sodium bicarbonate solution, aqueous sodium chloride solution, and water. The mixture then was dried over magnesium sulfate. The mixture was concentrated, and ethanol was added to the residue. The product crystallized upon scratching of the vessel wall. The solid was filtered and washed with a mixture of ethanol and ether. The solid was air dried to obtain 7.2 g. of product, m.p. 118°-120° C. Thin layer chromatography (TLC) showed the presence of a trace of starting material.

Analysis, Calcd. for $C_{22}H_{16}O_3S$: C, 73.31; H, 4.47; O, 13.32 Found: C, 73.58; H, 4.41; O, 13.30.

EXAMPLE 3

Preparation of 2-(4-hydroxybenzoyl)-3-phenylbenzothiophene.

A mixture of 12.0 g. of the product from Example 1 and 35 g. of pyridine hydrochloride was refluxed for 30 minutes. The hot reaction mixture then was poured over ice, and the mixture was transferred to a blender, homogenized, and the resulting crystals were collected by filtration, washed with water, and dried in vacuo at 80° C. to give 11.0 g. (96 percent) of the title compound, m.p. 204°-205° C.

Analysis, Calcd. for $C_{21}H_{14}O_2S$: C, 76.34; H, 4.27; S, 9.70. Found: C, 76.11; H, 4.22; S, 10.00.

EXAMPLES 4

Preparation of 2-(4-Hydroxybenzoyl)-3-phenylbenzothiophene-1-oxide.

The product from Example 3 (5.0 g.; 0.0151 mole) and 2.8 g. of m-chloroperbenzoic acid were dissolved together in chloroform. The mixture was allowed to stand at room temperature for about 3 days. The solution then was washed twice with aqueous sodium bicarbonate solution, then with water, and was dried over magnesium sulfate. The solution then was concentrated to dryness. Thin-layer chromatography (TLC) run on the crude product revealed the presence of the starting material, some sulfone, and the desired product. The mixture was slurried in hot benzene, allowed to cool, and filtered to obtain 2.6 g. of a material having m.p. 140°-145° C. TLC on this product indicated some sulfone was still present. The solid was slurried in benzene, warmed, and filtered while hot. The collected solid then was slurried in benzene containing a small amount of ethanol, heated, and allowed to cool. The title compound (1.3 g.) crystallized out and was collected by filtration. TLC of this product indicated the presence only of traces of the sulfone contaminant. The melting point of the product was 215° C. The product was dried in vacuo at 120° C. overnight to further remove any solvent which might be present.

Analysis, Calcd. for $C_{21}H_{14}O_3S$: C, 72.81; H, 4.07 O, 13.86 Found: C, 73.06; H, 4.21; O, 13.80.

EXAMPLE 5

Preparation of 2-Benzoyl-3-phenyl-6-methoxybenzothiophene

To 100 ml. of 1,2-dichloroethane were added 5.0 g. (0.021 mole) of 3-phenyl-6-methoxybenzothiophene and 2.81 g. (0.021 mole) of benzoyl chloride. The mixture was cooled to 0° C., and 2.93 g. (0.022 mole) of aluminum chloride were added. The mixture was stirred for one hour, and ice then was added. The resulting organic layer was separated, washed with water, and evaporated. To the residue were added 250 ml. of methanol and 10 ml. of 5N sodium hydroxide. The mixture was refluxed for 30 minutes, evaporated, and ether and water were added to the residue. The ether layer was separated, washed with 1N sodium hydroxide, 1N hydrochloric acid, and aqueous soidum chloride. The ether layer then was dried over magnesium sulfate, filtered, and evaporated. The residue was crystallized from methanol to obtain 3.77 g. (52 percent) of the title compound, m.p. 94°-95.5° C.

Analysis, Calcd. for $C_{22}H_{16}O_2S$: C, 76.72; H, 4.68; O, 9.29; S, 9.31 Found: C, 76.51; H, 4.90; O, 9.08; S, 9.13

EXAMPLE 6

Preparation of
2-Benzoyl-3-phenyl-6-hydroxybenzothiophene

A mixture of 2.5 g. (0.0073 mole) of the product from Example 5 and 10 g. of pyridine hydrochloride was refluxed in a 220° C. oil bath for 1.5 hours. The hot reaction mixture then was poured over an ice-water mixture in a blender, and the resulting yellow crystals were collected. The crystals then were dissolved in ethyl acetate, and the ethyl acetate solution was washed with saturated aqueous sodium chloride and dried over magnesium sulfate. The ethyl acetate solution then was filtered over silica, and the silica was washed with ethyl acetate which was added to the original ethyl acetate solution. The ethyl acetate was evaporated and the resulting residue was crystallized from methanol to give 2.1 g. (88 percent) of the title compound as yellow crystals, m.p. 187°–190° C. The product was recrystallized from methanol to give a purified product having melting point 191°–191.5° C.

Analysis, Calcd. for $C_{21}H_{14}O_2S$: C, 76.34; H, 4.27; Found: C, 76.29; H, 4.03.

Mass spectrum (MS): Theory, 330; Found, 330.

EXAMPLE 7

Preparation of
2-(4-Methoxybenzoyl)-3-phenyl-6-methoxybenzothiophene

To 500 ml. of 1,2-dichloroethane were added 24.0 g. (0.10 mole) of 3-phenyl-6-methoxybenzothiophene and 17.1 g. (0.10 mole) of p-methoxybenzoyl chloride. The mixture was cooled to 0° C., and 13.4 g. (0.10 mole) of aluminum chloride were added. The mixture was stirred for 1 hour, and ice then was added to the mixture. The organic layer was separated, washed with water, and evaporated. To the residue were added a mixture of methanol and 5N sodium hydroxide. The mixture was refluxed for 30 minutes and evaporated. To the residue were added ether and water. The ether layer was separated, washed with 1N sodium hydroxide, 1N hydrochloric acid, and aqueous sodium chloride solution. The ether layer then was dried over magnesium sulfate, filtered, and evaporated to give crude product which was recrystallized from methanol to obtain 34.2 g. (91 percent) of the title compound, m.p. 127°–128° C.

Analysis, Calcd. for $C_{23}H_{18}O_3S$: C, 73.77; H, 4.85; O, 12.82; S, 8.56 Found: C, 74.17; H, 5.00; O, 12.93; S, 8.36.

EXAMPLE 8

Preparation of
2-(4-Hydroxybenzoyl)-3-phenyl-6-hydroxybenzothiophene

A mixture of 8.75 g. (0.023 mole) of the product from Example 7 and 25 g. of pyridine hydrochloride was prepared. The mixture was refluxed in a 220° C. oil bath for 30 minutes. The hot reaction mixture then was poured over ice, and the resulting mixture was added to a blender. The resulting yellow crystals were collected on a filter, washed with water, and vacuum dried at 100° C. This treatment caused some resinification of the sample. The residue was recrystallized from a mixture of ethyl acetate and benzene to obtain 5.3 g. (65 percent) of the title compound as bright yellow crystals, m.p. 198°–200° C.

EXAMPLE 9

Preparation of
2-(4-Methoxybenzoyl)-3-phenyl-6-methoxybenzothiophene-1-oxide.

To a solution of 1.1 g. (0.0206 mole) of the product from Example 7 in chloroform cooled to 0° C. were added dropwise 3.53 g. of m-chloroperbenzoic acid dissolved in chloroform. The temperature was maintained at 0° C. during addition. The mixture then was stirred at room temperature overnight. Thin-layer chromatography of a sample of the reaction mixture indicated the presence of starting material. The reaction mixture therefore was allowed to stir for three additional days. The mixture then was washed three times with 200 ml. each of aqueous sodium bicarbonate solution and once with water. The organic layer then was dried over magnesium sulfate and concentrated. The residue was dissolved in ethanol. The ethanol was cooled, and a small amount of acetone was added. The mixture was filtered to obtain 3.6 g. of product, m.p. 159°–160° C.

A TLC of this material indicated the presence of three spots, one of which corresponded to starting material. Therefore, the material was slurried in warm benzene, and the insoluble material was isolated by filtration. The collected material constituted nearly pure sulfoxide, the desired product. The product then was recrystallized from benzene to give the title compound in a highly pure state, m.p. 191°–192° C.

Analysis, Calcd. for $C_{23}H_{18}O_4S$: C, 70.75; H, 4.65; O, 16.39 Found: C, 70.77; H, 4.80 O, 16.23.

EXAMPLE 10

Preparation of
2-(4-Cyclopentyloxy)benzoyl-3-phenyl-6-hydroxybenzothiophene.

A. Preparation of p-cyclopentyloxybenzoyl chloride.

To 50 g. of methyl p-hydroxybenzoate were added 82 g. of cyclopentyl bromide. The mixture was cooled to 0° C., and 24 g. of sodium hydride (in a 50 percent mineral oil suspension) were added in small portions. Ice bath cooling was continued until the resulting effervescence terminated. The reaction mixture then was heated to 75° C. for four hours, cooled, and 25 ml. of ethanol were added dropwise. The resulting mixture was evaporated to dryness, and the residue was dissolved in a mixture of water and ether. The ether layer was separated and washed with cold 5 percent aqueous sodium hydroxide and then with water. The ether layer then was dried over magnesium sulfate and evaporated to dryness to give about 72 g. of crude methyl p-cyclopentyloxybenzoate.

The crude ester was added to 400 ml. of ethylene glycol containing 100 g. of potassium hydroxide. The mixture was refluxed for several hours and then was transferred to a 4 l. beaker. A mixture of ice and water was added. The resulting mixture then was placed in a 4 l. separatory funnel and was washed with ether. The aqueous layer was acidified by addition of concentrated hydrochloric acid. The resulting precipitate was collected by filtration, washed with water, and recrystallized from methanol to obtain 44.1 g. of p-cyclopentyloxybenzoic acid, m.p. 175° C.

Analysis, Calcd for $C_{12}H_{14}O_3$: C, 69.89; H, 6.84; O, 23.27 Found: C, 69.61; H, 6.86; O, 23.19.

A solution of 8.7 g. (0.024 mole) of p-cyclopentyloxybenzoic acid in 250 ml. of anhydrous ether was prepared. The solution was cooled to 5°-10° C., and 8.85 g. of thionyl chloride followed by two drops of pyridine were added. The mixture was allowed to warm to room temperature and was stirred overnight. The mixture then was evaporated to dryness, and the oily residue of p-cyclopentyloxybenzoyl chloride was dissolved in 150 ml. of 1,2-dichloroethane for use as described hereinbelow.

B. Acylation and demethylation of 3-phenyl-6-methoxybenzothiophene.

The above solution of p-cyclopentyloxybenzoyl chloride was cooled to 0° C., and 10 g. (0.0417 mole) of 3-phenyl-6-methoxybenzothiophene were added. To the resulting mixture then were added 5.7 g. (0.043 mole) of solid aluminum chloride. The mixture was stirred for one hour after which ice was added.

The organic layer was separated from the aqueous and was washed with water and evaporated. To the residue then were added a mixture of methanol and 5N sodium hydroxide. The mixture was refluxed for 30 minutes and evaporated. Ether and water were added to the residue. The ether layer was separated and washed successively with 1N sodium hydroxide, 1N hydrochloric acid, and aqueous sodium chloride solution. The ether layer then was dried over magnesium sulfate, filtered, and evaporated to obtain crude 2-(4-cyclopentyloxy)benzoyl-3-phenyl-6-methoxybenzothiophene.
The crude product was chromatographed over silica using benzene as eluant. Appropriate fractions gave about 6 g. of the crude product of sufficient purity to be employed in the next succeeding reaction step.

To 100 ml. of dry N,N-dimethylformamide were added 5.0 g. (0.014 mole) of the crude benzothiophene obtained hereinabove and 1.2 g. (0.05 mole) of sodium hydride. The mixture was cooled to 0° C. under nitrogen. Ethyl mercaptan (3.1 g.; 0.05 mole) was added to the mixture by means of a syringe. The addition of the ethyl mercaptan caused vigorous effervescence. When effervescence had ceased, the reaction mixture was heated at 90° C. overnight. To the resulting reaction mixture then were added dropwise 25 ml. of ethanol. The resulting mixture was evaporated to dryness, and the residue was dissolved in a mixture of water and ether. The ether layer was separated and washed with dilute hydrochloric acid and dilute sodium hydroxide. The ether layer then was dried over magnesium sulfate and evaporated to give a yellow oil which was chromatographed over silica using a solvent gradient ranging from 100 percent benzene to a mixture of 90 percent benzene and 10 percent ethyl acetate. The title compound (about 3 g.) was recovered from appropriate chromatograph fractions as a pale yellow foam.

Analysis, Calcd. for $C_{26}H_{22}O_3S$: C, 75.34; H, 5.35; O, 11.58; S, 7.74 Found: C, 75.61; H, 5.58; O, 11.43; S, 7.10.

EXAMPLE 11

Preparation of
2-(3-Methoxybenzoyl)-3-phenyl-6-methoxybenzothiophene

To 100 ml. of ether were added 3.18 g. (0.0208 mole) of m-methoxybenzoic acid. To the mixture were added 4.70 g. (0.04 mole) of thionyl chloride and 1 drop of pyridine. The resulting mixture was stirred at room temperature for 16 hours. The solvent was evaporated, and 100 ml. of dry benzene were added to the residue. The benzene was evaporated, and the residue, m-methoxybenzoyl chloride was dissolved in 100 ml. of 1,2-dichloroethane.

To the resulting dichloroethane solution, 5 g. (0.0208 mole) of 3-phenyl-6-methoxybenzothiophene were added. The mixture was cooled to 0° C., and 2.8 g. (0.021 mole) of aluminum chloride were added. The mixture was maintained at 0° C. for one hour, and the reaction mixture was worked up in accordance with the procedure delineated in Example 6. The product was recrystallized from methanol to obtain 6.37 g. (82 percent) of the title compound, m.p. 101°-103° C.

Analysis, Calcd. for $C_{23}H_{18}O_3S$: C, 73.27; H, 4.85; O, 12.82; S, 8.56 Found: C, 74.14; H, 4.83; O, 12.38; S, 8.48

EXAMPLE 12

Preparation of
2-(3-Hydroxybenzoyl)-3-phenyl-6-hydroxybenzothiophene.

Employing the procedure of Example 7, 5.0 g. (0.0134 mole) of the product from Example 11 was demethylated by treatment with 25 g. of pyridine hydrochloride for three hours in a 220° C. oil bath. Yellow crystals, obtained from ethyl acetate, were recrystallized from a mixture of 20 ml. of methanol and about 12 ml. of water to give 4.184 g. (91 percent) of the title compound as yellowish-brown crystals. Melting point 202.0°-202.5° C.

Analysis, Calcd. for $C_{21}H_{14}O_3S$: C, 72.81; H, 4.07; O, 13.86; S, 9.26 Found: C, 72.70; H, 3.94; O, 13.57; S, 9.50.

Mass spectrum: Theory, 346; Found, 346.

EXAMPLE 13

Preparation of
2-(2-Hydroxybenzoyl)-3-phenyl-6-hydroxybenzothiophene

By the procedure of Example 5, 5.0 g. (0.0208 mole) of 3-phenyl-6-methoxybenzothiophene were treated with 3.60 g. (0.021 mole) of o-methoxybenzoyl chloride and 2.80 g. (0.021 mole) of aluminum chloride in 100 ml. of 1,2-dichloroethane as solvent. The crystalline product, 2-(2-methoxybenzoyl)-3-phenyl-6-methoxybenzothiophene (7.52 g.; 97 percent) was obtained from methanol, m.p. 111°-112° C. The product was sufficiently pure to be employed in the next succeeding step; however, a portion of the product was further purified by recrystallization from methanol with the following analytical result.

Analysis, Calcd. for $C_{23}H_{18}O_3S$: C, 73.77; H, 4.85; O, 12.82 Found: C, 73.96; H, 4.77; O, 12.60.

Employing the procedure of Example 6, 5.5 g. (0.0147 mole) of the above product was demethylated by treatment with 25 g. of pyridine hydrochloride in a 220° C. oil bath for three hours. The product, obtained from the ethyl acetate solution, was an oil which exhibited two spots on TLC. Therefore, the product was dissolved in 1N sodium hydroxide, and the sodium hydroxide solution was washed several times with ether and ethyl acetate. Upon acidification of the 1N sodium hydroxide solution, 4.5 g. of the title compound were collected as an oil.

Analysis, Calcd. for $C_{21}H_{14}O_3S$: C, 72.81; H, 4.07; O, 13.86; S, 9.26 Found: C, 72.88; H, 4.19; O, 13.77; S, 8.58.

Mass Spectrum: Calcd., 346; Found 346.

The product was crystallized from benzene and recrystallized from a 2:1 mixture of benzene and hexane to obtain 3.57 g. of crystalline product, m.p. 123°–124° C.

EXAMPLE 14

Preparation of the citrate salt of 2-(4-methoxybenzoyl)-3-[4-(2-pyrrolidinoethoxy)-phenyl]-6-methoxybenzothiophene.

To 80 ml. of N,N-dimethylformamide (DMF) were added 10.0 grams (0.039 mole) of 3-(4-hydroxyphenyl)-6-methoxybenzothiophene. The mixture was cooled to 0° C., and 6.6 grams (0.039 mole) of N-(2-chloroethyl)-pyrrolidine hydrochloride were added followed by 2.81 grams (0.117 mole) of sodium hydride added in small portions. Effervescence developed, and, when the effervescence had ceased, the mixture was heated at 95° C. for 14 hours. To the mixture then were added 10 ml. of ethanol, and the solvents of the resulting mixture then were evaporated. The resulting residue was dissolved in a mixture of water and ethyl acetate. The ethyl acetate layer was separated from the aqueous layer and was washed with 25 ml. of sodium chloride solution. The ethyl acetate solution then was extracted twice with 40 ml. of 1N hydrochloric acid. The acid layer was separated and rendered alkaline by addition of 50 ml. of 2N sodium hydroxide. The alkaline mixture then was extracted with 250 ml. of ethyl acetate. The ethyl acetate layer was separated, dried over magnesium sulfate, and evaporated to give 3-[4-(2-pyrrolidinoethoxy)phenyl]-6-methoxybenzothiophene as an oil. The oil was dissolved in methanol and treated with excess methanolic hydrochloric acid. The mixture was evaporated, and the solid residue was recrystallized from methanol to give 11.6 grams (76 percent) of the hydrochloride salt of 3-[4-(2-pyrrolidinoethoxy)phenyl]-6-methoxybenzothiophene, m.p. 200°–202° C.

The free base was generated from 8.0 grams (0.0205 moles) of the above hydrochloride salt by adding the hydrochloride salt to 20 ml. of 2N sodium hydroxide at 0° C. and extracting the thus-produced free base with 250 ml. of chloroform. The chloroform layer was separated, dried over magnesium sulfate, filtered, and evaporated. The residual base then was dissolved in 200 ml. of 1,2-dichloroethane. The mixture was cooled to 0° C., and 2.80 grams (0.021 mole) of aluminum chloride were added. To the resulting solution then were added 3.58 grams (0.021 mole) of p-methoxybenzoyl chloride followed by an additional 2.80 grams (0.021 mole) of aluminum chloride. The resulting mixture, a dark red solution, was stirred at room temperature for 72 hours. Ice and 30 ml. of 5N sodium hydroxide then were added to the mixture. The organic layer was separated and evaporated to dryness. To the resulting residue were added 250 ml. of methanol and 25 ml. of 5N sodium hydroxide. The resulting mixture was heated on a steam bath for 15 minutes, evaporated, and ethyl acetate and water were added to the residue. The ethyl acetate layer was separated, washed with two 100 ml. portions of aqueous sodium chloride solution, dried over magnesium sulfate, and evaporated to give about 11 grams of the free base of the title compound as a yellow oil.

The oil was dissolved in 20 ml. of warm methyl ethyl ketone (MEK), and the solution then was added to a solution of 4.41 grams (0.02. mole) of citric acid monohydrate in 50 ml. hot MEK. An oil separated. Ether was added in an amount sufficient to provide a total volume of about 300 ml. The mixture was allowed to stand overnight, and pale yellow crystals formed which were collected by filtration, washed with ether, and recrystallized by dissolving them in about 1400 ml. of hot acetone, filtering the acetone solution, and concentrating the filtrate to about 200 ml. The title compound was obtained (11.4 grams; 82 percent) as cream colored crystals, m.p. 128°–131° C.

Mass spectrum: Theory (free base), 487; Found: 487. Analysis, Calcd. for $C_{35}H_{37}NO_{11}S$: C, 61.84; H, 5.49; N, 2.06; O, 25.89; S, 4.72. Found: C, 62.56; H, 5.72; N, 2.19; O, 23.25; S, 5.67.

The product was further purified by regenerating and slurrying 11 grams of the free base in 200 ml. of 2N sodium hydroxide at room temperature for 15–20 minutes. The mixture was filtered, and the solid was washed several times with water and dried in vacuo overnight. One-half of the free base was dissolved in acetone, and the insoluble material was separated by gravity filtration. One equivalent of citric acid in hot acetone was added to the acetone filtrate. The mixture was cooled, and the title compound was collected by filtration and dried in vacuo, m.p. 126°–128° C.

Analysis, Calcd. for $C_{35}H_{37}NO_{11}S$: C, 61.84; H, 5.49; N, 2.06; O, 25.89. Found: C, 62.04; H, 5.33; N, 1.79; O, 25.54.

EXAMPLE 15

Preparation of 2-(4-Hydroxybenzoyl)-3-phenyl-5-hydroxybenzothiophene.

A. Preparation of m-methoxybenzophenone.

To one liter of anhydrous ether were added 187 grams (1 mole) of m-bromoanisole, 48 grams (2 mole) of magnesium, and 0.5 ml. of 1,2-dibromoethane. The mixture was stirred at room temperature for four hours during which time a considerable amount of insoluble magnesium bromide was in evidence.

To the mixture then were added dropwise 103 grams (1 mole) of benzonitrile in 500 ml. of ether. A vigorous reaction occurred. The mixture was stirred for 16 hours, and then 500 ml. of water were gradually added. The reaction mixture then was filtered through a glass wool plug to remove excess magnesium. The ether was evaporated, and to the resulting aqueous layer were added 300 ml. of concentrated hydrochloric acid. The resulting mixture was heated on a steam bath for one hour. The product was extracted into ether, and the ether layer was washed with water, dried, and distilled to obtain 127 grams (60 percent) of m-methoxybenzophenone as a pale green liquid, b.p. 135°–139°/0.05 mm.

Analysis, Calcd. for $C_{14}H_{12}O_2$: C, 79.23; H, 5.70; O, 15.08. Found: C, 78.96; H, 5.91; O, 14.93.

B. Preparation of phenyl m-methoxyphenyl ketimine.

To 125 grams (0.59 mole) of the product from Part A in three liters of benzene at about 10° C. were added dropwise 56.7 grams (0.30 mole) of titanium tetrachloride. A red-orange complex formed in the benzene solution. Anhydrous ammonia then was rapidly bubbled into the mixture, and the temperature of the mixture rose to 30° C. As the ammonia was added, the color of the mixture progressively changed from red-orange to yellow to green and then to yellow. The ammonia addition then was stopped, and the reaction mixture was stirred overnight, during which time it became colorless. The resulting solids were filtered off, and the benzene filtrate was evaporated to give 125 grams (100 percent) of the title compound as a pale green oil.

C. Preparation of 5-(α-m-Methoxyphenylbenzylidene)-rhodanine.

To 1 l. of toluene were added 125 grams (0.59 mole) of the product from Part B, 80 grams (0.6 mole) of rhodanine, and 2 ml. of acetic acid. The mixture was refluxed for two hours. The toluene then was evaporated, and the residue was dissolved in 1.5 liters of ethyl acetate. The ethyl acetate solution was washed with water and then 250 ml. portions of 1N sodium hydroxide at 0° C. The ethyl acetate layer then was dried over magnesium sulfate and evaporated to give 176 grams of the title compounds as a red oil. The red oil would not crystallize; however, it was of sufficient purity to employ as such in the next succeeding step.

A small sample of the red oil was purified by being chromatographed over silica, employing as gradient eluant a system ranging from 100 percent benzene to a mixture of 10 percent ethyl acetate and 90 percent benzene.

Analysis, Calcd. for $C_{17}H_{13}NO_2S_2$: C, 62.36; H, 4.00; N, 4.28; O, 9.77; S, 19.56. Found: C, 62.38; H, 4.24; N, 4.21; O, 10.03; S, 19.20.

Mass Spectrum: Theory, 327; Found, 327.

D. Preparation of α-thiol-β-(3-methoxyphenyl)-cinnamic acid.

The product from Part C (175 grams; 0.53 mole) was heated on a steam bath with 5N sodium hydroxide and 400 ml. of water until all starting material was gone as indicated by TLC. Total heating time was about 2 hours. The reaction mixture then was diluted to 5 liters by addition of water, and the reaction mixture was washed with one liter of ethyl acetate. The aqueous alkaline layer was separated, cooled to 0° C., and acidified by addition of an excess of 50 percent hydrochloric acid. A yellow oil separated and crystallized. The crystals were collected, washed with water, and vacuum dried to give 96.3 grams (64 percent) of the title compound. A sample of the product was recrystallized from a mixture of methanol and water for analytical purposes, m.p. 152–153° C.

Analysis, Calcd. for $C_{16}H_{14}O_3S$: C, 67.11; H, 4.93; O, 16.76; S, 11.20. Found: C, 67.09; H, 4.99; O, 16.62; S, 11.17.

Mass Spectrum: Theory, 284; Found, 284.

E. Preparation of 2-Carboxy-3-phenyl-5-methoxybenzothiophene.

The product from the Part D (35 grams; 0.122 mole) was dissolved in a minimum of benzene at 25° C. and was treated with 122 ml. of a 1.0 molar solution of chlorine in carbon tetrachloride. The mixture was stirred for two days and then was evaporated to dryness to give crude, oily, yellow crystals. Trituration of the solid in ethyl acetate gave crystals. The crystals were recrystallized from methanol to give 4.8 grams (14%) of the title compound, melting point 220°–221° C.

Analysis Calcd. for $C_{16}H_{18}O_3S$: C, 67.59; H, 4.25; O, 16.88; S, 11.28. Found: C, 67.60; H, 4.42; O, 16.39; S, 11.11.

Mass spectrum: Theory, 284; Found, 284.

F. Preparation of 2-(4-methoxybenzoyl)-3-phenyl-5-methoxybenzothiophene.

To 100 ml. of anhydrous ether were added 4.53 grams (0.016 mole) of the product from Part E. To the resulting solution then were added 4.15 grams (0.035 mole) of thionyl chloride and one drop of pyridine. The resulting mixture was stirred at 25° C. for 12 hours. The ether and excess thionyl chloride were evaporated, and 50 ml. of anhydrous benzene were added to the residue. The benzene mixture was evaporated to dryness, and the benzene step was repeated.

The residue, the acid chloride of the starting material, then was cooled to 0° C. and dissolved in 100 ml. of 1,2-dichloroethane. Anisole (1.78 grams; 0.0.65 mole) was added followed by 2.20 grams (0.0165 mole) of aluminum chloride. The mixture was stirred at 0° C. for 1 hour. The reaction then was quenched by addition of ice. The resulting organic layer was separated, washed with water, dried over magnesium sulfate, and evaporated to give an oil which failed to crystallize but which gave a single spot on TLC. The product then was chromatographed. Fractions 10–17 gave 5.29 grams (88 percent) of the title compound, m.p. 137°–138° C.

Analysis, Calcd. for $C_{23}H_{18}O_3S$: C, 73.77; H, 4.85; O, 12.82; S, 8.56. Found: C, 74.33; H, 4.77; O, 12.65; S, 8.31.

Mass Spectrum: Theory, 374; Found, 374.

G. Preparation of 2-(4-hydroxybenzoyl)-3-phenyl-5-hydroxybenzothiophene.

By the procedure of Example 7, 4.0 grams (0.0107 mole) of the product from Part F were treated with 20 g. of pyridine hydrochloride in a 220° C. oil bath for 3 hours. The title compound (3.30 grams; 89 percent) was obtained from a 1:1 mixture of methanol and water as brownish-yellow crystals, m.p. 231°–232° C.

Analysis, Calcd. for $C_{21}H_{14}O_3S$: C, 72.81; H, 4.07; O, 13.86; S, 9.26. Found: C, 72.83; H, 4.11; O, 13.86; S, 9.02.

Mass Spectrum: Theory, 346; Found, 346.

EXAMPLE 16

Preparation of 2-(3-Chlorobenzoyl)-3-phenyl-6-methoxybenzothiophene.

To 200 ml. of 1,2-dichloroethane were added 10.0 g. (0.042 mole) of 3-phenyl-6-methoxybenzothiophene and 6.5 g. (0.042 mole) of 3-chlorobenzoyl chloride. The mixture was stirred and cooled to 0° C., and 5.73 g. (0.042 mole) of aluminum chloride were added. The mixture was stirred for about one hour and ice then was added. The resulting organic layer was separated from the aqueous. The aqueous layer was washed with chloroform, and the chloroform was separated and added to the organic layer. The organic layer then was evaporated, and to the resulting residue were added 250 ml. of methanol and 15 ml. of 5N sodium hydroxide. The mixture was refluxed for 30 minutes and evaporated. The residue was recrystallized from methanol to obtain the title compound, m.p. 105° C.

Analysis, Calcd. for $C_{22}H_{15}O_2SCl$: C, 69.74; H, 3.99; O, 8.45; S, 8.46. Found: C, 70.01; H, 3.91; O, 8.60; S, 8.96.

EXAMPLE 17

Preparation of 2-(3-Chlorobenzoyl)-3-phenyl-6-hydroxybenzothiophene.

A mixture of 10.9 g. of the product from Example 16 and 33.6 g. of pyridine hydrochloride was refluxed in a 220° C. oil bath for 1.5 hours. The hot reaction mixture then was poured over an ice-water mixture, and the resulting solid was collected. The solid was washed with water and dissolved in ethyl acetate. The ethyl acetate solution was washed with saturated aqueous sodium chloride and dried over magnesium sulfate. The ethyl acetate solution then was filtered and evaporated. The residue was recrystallized from a mixture of metha-

21 nol and a minimum of acetone to give 5.07 g. (39 percent) of the title compound, m.p. 215° C.

Analysis, Calcd. for $C_{21}H_{13}O_2SCl$: C, 69.13; H, 3.59; O, 8.77; Cl, 9.72. Found: C, 68.90; H, 3.77; O, 9.15; Cl, 9.69.

EXAMPLE 18

Preparation of 2-(4-Chlorobenzoyl)-3-phenyl-6-methoxybenzothiophene.

To 200 ml. of 1,2-dichloroethane were added 10 g. (0.042 mole) of 3-phenyl-6-methoxybenzothiophene and 6.5 g. (0.042 mole) of 4-chlorobenzoyl chloride. The mixture was cooled to 0° C., and 5.73 g. of aluminum chloride were added. The mixture was stirred overnight, and an additional 10 percent of 4-chlorobenzyl chloride and aluminum chloride was added. The reaction mixture was maintained for approximately one hour, and ice then was added to the mixture. The resulting organic layer was separated from the aqueous, the aqueous layer was washed with chloroform which was then added to the organic layer. The organic layer was evaporated to dryness. To the resulting residue were added 250 ml. of methanol and 15 ml. of 5N sodium hydroxide. The mixture was refluxed for 40 minutes and then was evaporated. The residue was dissolved in ethyl acetate, and the ethyl acetate solution was washed successively with water and aqueous sodium chloride. The organic layer was dried over magnesium sulfate, filtered, and evaporated to give the title compound, m.p. 115° C.

EXAMPLE 19

Preparation of 2-(4-Chlorobenzoyl)-3-phenyl-6-hydroxybenzothiophene.

A mixture of 7 g. of the product from Example 18 and 27 g. of pyridine hydrochloride was refluxed in a 220° C. oil bath for 1.5 hours. The hot reaction mixture then was poured over an ice-water mixture. The resulting solid was collected and dissolved in ethyl acetate. The ethyl acetate solution was washed with saturated aqueous sodium chloride and dried over magnesium sulfate. The ethyl acetate solution was evaporated, and the residue was recrystallized from methanol to give 3.59 g. of the title compound, m.p. 222° C.

Analysis, Calcd. for $C_{21}H_{13}O_2SCl$: C, 69.13; H, 3.59; O, 8.77; S, 8.79; Cl, 9.72. Found: C, 68.96; H, 3.73; O, 9.15; S, 8.90; Cl, 9.66.

The compounds of this invention are tested for antifertility activity in accordance with the following procedure:

Fifty young adult virgin female rats weighing 200–230 g. each are separated into ten groups of five each. One of the groups serves as the control group and the other nine groups as experimental groups, each such experimental group receiving test compound at a particular dose level. The test compound for each group of five rats is prepared in corn oil such that the daily administration is in 0.1 ml. of vehicle. The designated quantity of the test compound in the vehicle is administered to each rat within the defined group subcutaneously (sc) daily. The control group receives only the vehicle. Administration of the vehicle or the combination of test compound and vehicle is continued on a daily basis for 15 days. On the 5th day of treatment, two adult male rats weighing at least 250 g. each are added to each group, and cohabitation is continued until the 15th day at which time the male rats are withdrawn from the group. Each group of female rats then is maintained for an additional seven days after which the rats are sacrificed and examined for the presence of viable or resorbing fetuses.

The number of animals that exhibit evidence of pregnancy over the number of animals in the group is the pregnancy ratio. A compound is considered active when the ratio is 0/5 or 1/5. A ratio of 2/5 constitutes marginal activity, and anything higher is inactive.

The Table following illustrates the antifertility activity of compounds of this invention.

Table

Antifertility Activity

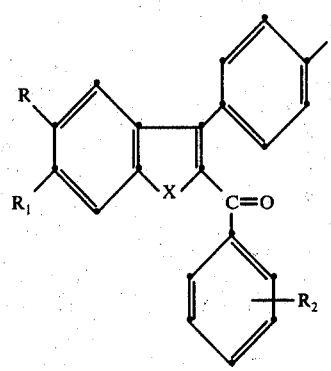

| R | $R_1$ | $R_2$ | $R_3$ | X | Dose mg./day | Pregnancy Ratio P/5 P= |
|---|---|---|---|---|---|---|
| H | —OCH$_3$ | H | H | S | 5.0 | 0 |
|  |  |  |  |  | 1.0 | 3 |
| H | H | —OCH$_3$ | H | S | 5.0 | 0[a] |
|  |  |  |  |  | 1.0 | 0 |
|  |  |  |  |  | 0.5 | 2 |
|  |  |  |  |  | 0.1 | 5 |
| H | —OH | H | H | S | 1.0 | 0 |
|  |  |  |  |  | 0.1 | 1 |
|  |  |  |  |  | 0.05 | 4 |
| H | H | 4-OH | H | S | 1.0 | 0 |
|  |  |  |  |  | 0.5 | 0 |
|  |  |  |  |  | 0.1 | 5 |
| H | —OCH$_3$ | 4-OCH$_3$ | H | S | 1.0 | 0 |
|  |  |  |  |  | 0.5 | 0 |
|  |  |  |  |  | 0.1 | 3 |
|  |  |  |  |  | 0.5 | 3 |
| H | —OCH$_3$ | 3-OCH$_3$ | H | S | 5.0 | 0 |
|  |  |  |  |  | 0.5 | 2 |
|  |  |  |  |  | 0.1 | 4 |
| H | —OH | 4-OH | H | S | 0.1 | 0 |
|  |  |  |  |  | 0.5 | 0 |
|  |  |  |  |  | 0.01 | 2 |
|  |  |  |  |  | 0.005 | 5 |
| —OH | H | 4-OH | H | S | 0.5 | 0 |
|  |  |  |  |  | 0.1 | 0[b] |
|  |  |  |  |  | 0.05 | 0 |
|  |  |  |  |  | 0.01 | 4 |
|  |  |  |  |  | 0.005 | 3 |
| H | —OH | 3-OH | H | S | 0.1 | 0 |
|  |  |  |  |  | 0.05 | 0 |
|  |  |  |  |  | 0.01 | 4 |

Table-continued

Antifertility Activity

| R | $R_1$ | $R_2$ | $R_3$ | X | Dose mg./day | Pregnancy Ratio P/5 P= |
|---|---|---|---|---|---|---|
| H | —OH | 2-OH | H | S | 0.005 | 5 |
|   |   |   |   |   | 0.5 | 0 |
|   |   |   |   |   | 0.1 | 2 |
|   |   |   |   |   | 0.05 | 2[c] |
| H | —OCH$_3$ | 4-OCH$_3$ | —OC$_2$H$_4$—N⟩ | S | 1.0 | 0 |
|   |   |   |   |   | 0.5 | 1 |
|   |   |   |   |   | 0.1 | 5 |
| H | —OH | 4-O—⟩ | H | S | 0.05 | 0 |
|   |   |   |   |   | 0.01 | 4 |
| H | H | 4-OCH$_3$ | H | SO | 5.0 | 0 |
|   |   |   |   |   | 1.0 | 4 |
| H | H | 4-OH | H | SO | 1.0 | 4[d] |
| H | —OCH$_3$ | 4-OCH$_3$ | H | SO | 1.0 | 0 |
|   |   |   |   |   | 0.5 | 0 |
|   |   |   |   |   | 0.1 | 1 |
|   |   |   |   |   | 0.05 | 4 |
| H | —OH | 3-Cl | H | S | 5.0 | 0 |
|   |   |   |   |   | 0.5 | 0 |
|   |   |   |   |   | 0.05 | 2 |
| H | —OH | 4-Cl | H | S | 5.0 | 0 |
|   |   |   |   |   | 1.0 | 3 |

Footnotes.
[a]Pregnancy ratio is 0/10.
[b]Pregnancy ratio is 0/4.
[c]Pregnancy ratio is 2/4.
[d]Although this compound appears to lack antifertility activity, an increase in dose would certainly establish such activity. Estrogenic testing of this compound at 5.0 mg/day shows strong activity which, based upon a comparison with the results from other active compounds in the series, is indicative of the presence of antifertility activity.

We claim:

1. A compound of the formula

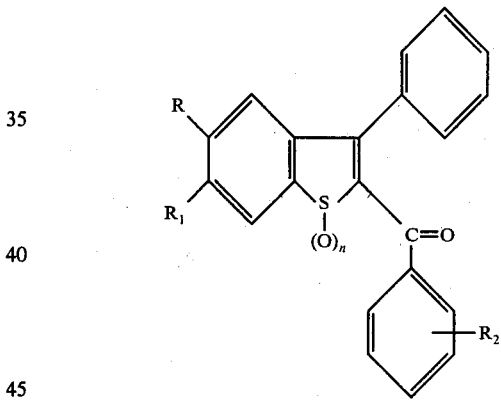

in which $n$ is 0 or 1; R and $R_1$ independently are hydrogen, hydroxyl, $C_1$- to $C_5$-alkoxy, or $C_5$- to $C_6$-cycloalkoxy; subject to the limitation that at least one of R and $R_1$ is hydrogen; $R_2$ is hydrogen, chloro, bromo, hydroxyl, $C_1$- to $C_5$-alkoxy, or $C_5$- to $C_6$-cycloalkoxy; subject to the limitation that at least one of R, $R_1$, or $R_2$ is other than hydrogen.

2. Compound of claim 1, in which $n$ is zero.
3. Compound of claim 2, in which $R_1$ is hydroxyl.
4. Compound of claim 2, in which $R_2$ is hydroxyl.
5. Compound of claim 4, in which the $R_2$ substituent is in the para position.
6. Compound of claim 3, in which $R_2$ is hydroxyl in the para position.
7. Compound of claim 3, in which $R_2$ is hydroxyl in the meta position.
8. Compound of claim 1, in which $n$ is 1.

* * * * *